US012575935B2

(12) United States Patent
Duma et al.

(10) Patent No.: US 12,575,935 B2
(45) Date of Patent: Mar. 17, 2026

(54) 3D PRINTED STRUCTURALLY SOUND PROSTHETIC SOCKET

(71) Applicant: Precision Valve & Automation, Inc., Halfmoon, NY (US)

(72) Inventors: Eric Stephen Duma, Wilton, NY (US); Jason Curtis Schoen, Clifton Park, NY (US); Karin Cecilia Backlin Schaffer, Loudonville, NY (US)

(73) Assignee: PRECISION VALVE & AUTOMATION, INC., Halfmoon, NY (US)

( * ) Notice: Subject to any disclaimer, the term of this patent is extended or adjusted under 35 U.S.C. 154(b) by 926 days.

(21) Appl. No.: 17/748,760

(22) Filed: May 19, 2022

(65) Prior Publication Data

US 2022/0370202 A1     Nov. 24, 2022

Related U.S. Application Data

(60) Provisional application No. 63/191,388, filed on May 21, 2021.

(51) Int. Cl.
| | |
|---|---|
| *A61F 2/80* | (2006.01) |
| *A61F 2/30* | (2006.01) |

(Continued)

(52) U.S. Cl.
CPC .......... *A61F 2/3094* (2013.01); *B29C 64/118* (2017.08); *B29C 64/209* (2017.08); *B33Y 10/00* (2014.12); *B33Y 30/00* (2014.12); *B33Y 80/00* (2014.12); *A61F 2002/30985* (2013.01);

*B29K 2995/0026* (2013.01); *B29L 2031/7532* (2013.01); *B33Y 70/00* (2014.12)

(58) Field of Classification Search
CPC .......... A61F 2/30942; A61F 2002/5049; A61F 2002/505; A61F 2002/5055; A61F 2/80; A61F 2/5046–2002/5052
See application file for complete search history.

(56) References Cited

U.S. PATENT DOCUMENTS

| | | |
|---|---|---|
| 6,689,171 B2 | 2/2004 | Slemker et al. |
| 10,850,442 B1 | 12/2020 | Miller |

(Continued)

FOREIGN PATENT DOCUMENTS

| | | |
|---|---|---|
| CN | 109199651 A | 1/2019 |
| WO | 2021032225 A1 | 2/2021 |

*Primary Examiner* — Alvin J Stewart
(74) *Attorney, Agent, or Firm* — Schmeiser, Olsen & Watts LLP

(57) ABSTRACT

A method for 3D printing a prosthetic socket from a digital model, including printing a solid wall perimeter of the prosthetic socket with a width achieved in a single pass of a printing nozzle, and forming a plurality of stiffener elements proximate a bottom end of the prosthetic socket, as a function of the printing the solid wall perimeter, is provided. Also provided is a 3D printed prosthetic socket including an upper portion, a lower portion configured to be attached to a prosthetic pylon, and a plurality of stiffener elements radially extending from the lower portion, wherein the upper portion, the lower portion, and the plurality of stiffener elements are printed as a solid wall construction comprised of a printing material deposited using only a single pass of a printing nozzle.

15 Claims, 14 Drawing Sheets

(51) Int. Cl.

| | |
|---|---|
| B29C 64/118 | (2017.01) |
| B29C 64/209 | (2017.01) |
| B33Y 10/00 | (2015.01) |
| B33Y 30/00 | (2015.01) |
| B33Y 80/00 | (2015.01) |
| B29L 31/00 | (2006.01) |
| B33Y 70/00 | (2020.01) |

(56) References Cited

U.S. PATENT DOCUMENTS

| | | | | |
|---|---|---|---|---|
| 10,905,568 | B2* | 2/2021 | Erenstone | B29C 64/386 |
| 11,957,604 | B2* | 4/2024 | Schaffer | B33Y 80/00 |
| 2004/0204770 | A1* | 10/2004 | Curtis | A61F 2/76 |
| | | | | 623/33 |
| 2010/0042227 | A1* | 2/2010 | Schmidt | A61F 2/80 |
| | | | | 623/36 |
| 2010/0161076 | A1* | 6/2010 | Pallari | A43B 13/183 |
| | | | | 700/98 |
| 2010/0228361 | A1* | 9/2010 | Radzinsky | A61F 2/80 |
| | | | | 623/33 |
| 2011/0015761 | A1* | 1/2011 | Celebi | A61F 2/80 |
| | | | | 623/32 |
| 2011/0112657 | A1* | 5/2011 | Haun | A61F 2/80 |
| | | | | 623/38 |
| 2014/0188260 | A1* | 7/2014 | Layman | A61F 2/5046 |
| | | | | 700/98 |
| 2015/0094824 | A1* | 4/2015 | Pommier | B29C 48/022 |
| | | | | 623/36 |
| 2016/0143752 | A1* | 5/2016 | Hurley | A61F 2/5046 |
| | | | | 156/60 |
| 2016/0192877 | A1* | 7/2016 | Diez | A61F 2/5046 |
| | | | | 602/5 |
| 2017/0105852 | A1* | 4/2017 | Chabloz | A61F 2/80 |
| 2017/0246013 | A1* | 8/2017 | Erenstone | B33Y 50/00 |
| 2017/0360578 | A1 | 12/2017 | Shin et al. | |
| 2018/0235779 | A1* | 8/2018 | Dudding | A61F 2/7812 |
| 2018/0243111 | A1 | 8/2018 | Hand | |
| 2018/0368996 | A1* | 12/2018 | Van Vliet | A61F 2/80 |
| 2020/0170811 | A1 | 6/2020 | Smith et al. | |
| 2020/0337871 | A1* | 10/2020 | Harmon | A61F 2/5046 |
| 2020/0345521 | A1 | 11/2020 | Mahon et al. | |
| 2023/0016023 | A1* | 1/2023 | Leiniger | B33Y 80/00 |
| 2025/0262071 | A1* | 8/2025 | Wagner | A61F 2/80 |

* cited by examiner

Conventional 3D Printing

SINGLE PASS METHOD OF 3D PRINTING

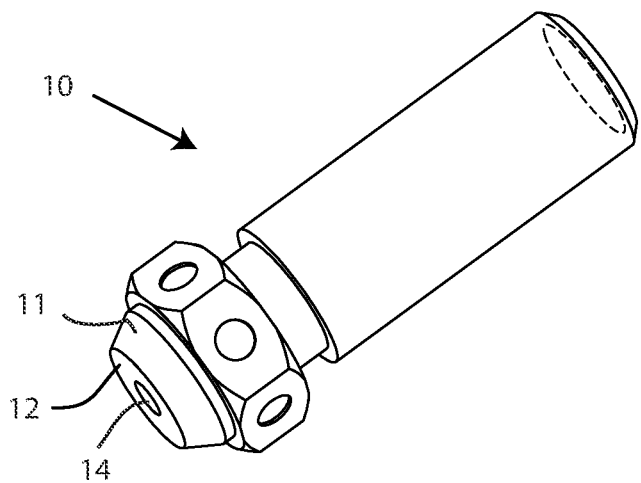
FIG. 2C
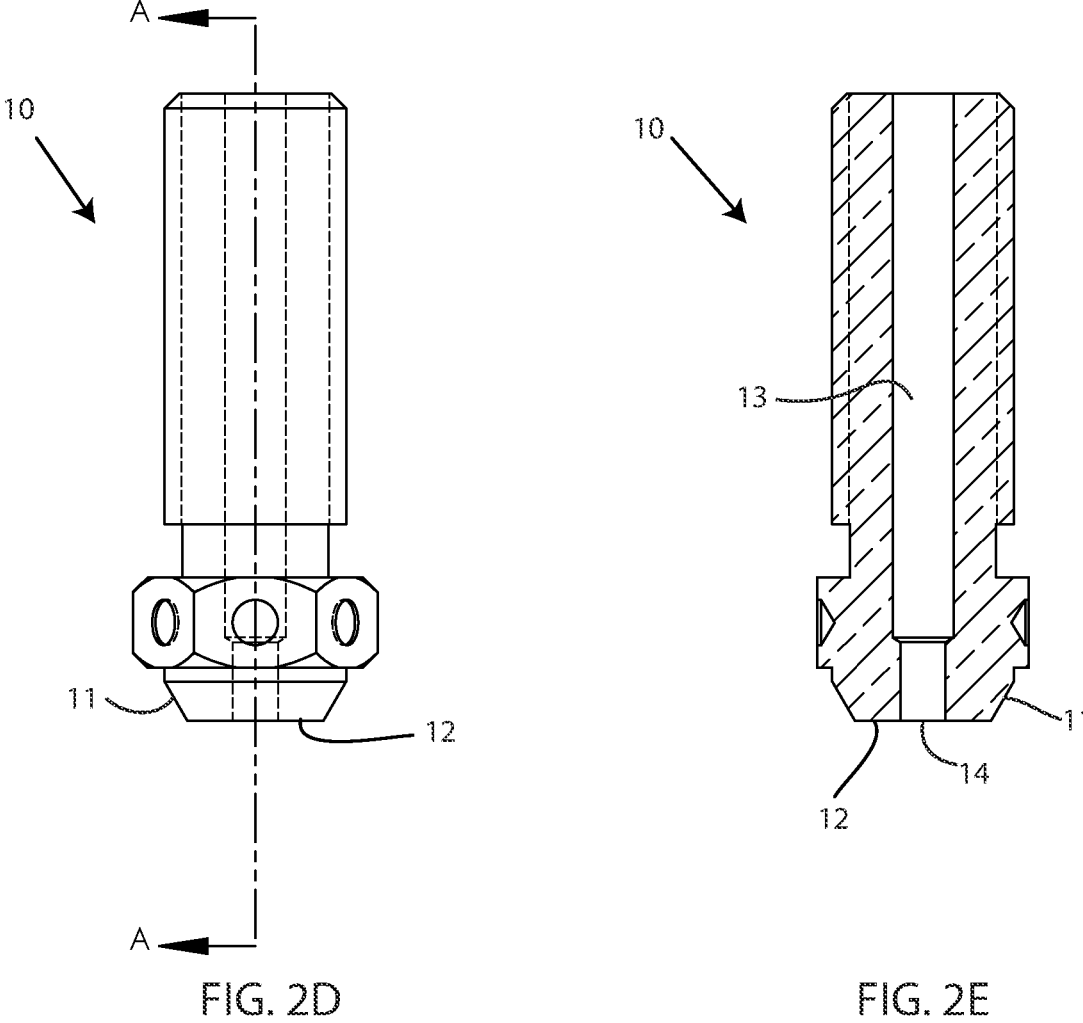
FIG. 2D                                             FIG. 2E

100

128

100

128

129

200

210

220

225

210

200

220

225

226

225

220

3D PRINTED STRUCTURALLY SOUND PROSTHETIC SOCKET

CROSS-REFERENCE TO RELATED APPLICATIONS

This application is a non-provisional application of and claim priority to U.S. Provisional Application No. 63/191,388, filed May 21, 2021, and entitled "3D Printed Structurally Sound Prosthetic Socket."

FIELD OF TECHNOLOGY

The following relates to embodiments of 3D printed prosthetic sockets, and more specifically to embodiments of a solid wall perimeter prosthetic socket and method of 3D printing the solid wall perimeter prosthetic socket.

BACKGROUND

Conventional methods of 3D printing are incapable of producing clear prosthetic sockets that allow for visual inspection. Further, conventional printing methods used for printing prosthetic sockets also lack a required structural strength to bear a user's weight. To reinforce the 3D printed prosthetic socket, additional hardware components that are not 3D printed along with the prosthetic socket must be attached to the prosthetic socket.

SUMMARY

An aspect relates to a method for 3D printing a prosthetic socket from a digital model, comprising: printing a solid wall perimeter of the prosthetic socket with a width achieved in a single pass of a printing nozzle, and forming a plurality of stiffener elements proximate a bottom end of the prosthetic socket, as a function of the printing the solid wall perimeter.

In an exemplary embodiment, the solid wall perimeter is printed in sequential layers or in a vase mode, and without voids.

In an exemplary embodiment, the solid wall perimeter is entirely comprised of an optically clear printing material, such as a transparent polycarbonate, polyethylene terephthalate glycol (PETG), polycylcohexylendimethylene terephthalate glycol (PCTG), polyactic acid (PLA), nylon, acrylonitrile butadiene styrene (ABS), polypropylene, and polyetherimide (PEI) based filament.

In an exemplary embodiment, the method also includes dispersing a deposited printing material using the printing nozzle to achieve a desired thickness of the solid wall perimeter in the single pass.

In an exemplary embodiment, the method optionally includes coating a surface of the prosthetic socket to improve clarity.

Another aspect relates to a 3D printed prosthetic socket comprising: an upper portion, a lower portion configured to be attached to a pylon, and a plurality of stiffener elements radially extending from the lower portion; wherein the upper portion, the lower portion, and the plurality of stiffener elements are printed as a solid wall construction comprised of a printing material deposited using only a single pass of a printing nozzle.

In an exemplary embodiment, the plurality of stiffener elements are disposed circumferentially around the lower portion. The plurality of stiffener elements can be the same shape or a different shape than another portion of the plurality of stiffener elements.

In an exemplary embodiment, the socket includes a bottom surface of the lower portion having at least one opening configured to receive hardware for fastening the 3D printed socket to a pylon.

In an exemplary embodiment, the upper portion, the lower portion, and the plurality of stiffener elements are comprised of an optically clear material, such as a transparent polycarbonate, polyethylene terephthalate glycol (PETG), polycylcohexylendimethylene terephthalate glycol (PCTG), polyactic acid (PLA), nylon, acrylonitrile butadiene styrene (ABS), polypropylene, and polyetherimide (PEI) based filament.

Another aspect relates to a 3D printing nozzle comprising: a nozzle body having a fluidic pathway therethrough; an outlet disposed at an end of the nozzle body, and a nozzle face adjacent to the outlet, the nozzle face configured to physically contact a deposited printed material to disperse the deposited printing material, wherein a diameter of the nozzle face is greater than a diameter of a filament being fed into the 3D printing nozzle.

In an exemplary embodiment, the nozzle face is a flat surface perpendicular to the fluidic pathway through which a printing material passes.

In an exemplary embodiment, the diameter of the nozzle face is at least 1.45 times larger than the diameter of the filament, the diameter of the nozzle face is between 1.45 and 2.25 times larger than the diameter of the filament, the diameter of the nozzle face is between 1.45-5 times larger than the diameter of the filament, or the diameter of the nozzle face is more than 5 times larger than the diameter of the filament.

Another aspect relates to sizing a nozzle face of a 3D printing nozzle based on a diameter of a filament being used together with the 3D printing nozzle. The method further comprising: manufacturing the 3D printing nozzle.

The foregoing and other features of construction and operation will be more readily understood and fully appreciated from the following detailed disclosure, taken in conjunction with accompanying drawings.

BRIEF DESCRIPTION OF THE DRAWINGS

Some of the embodiments will be described in detail, with reference to the following figures, wherein like designations denote like members, wherein:

FIG. 2C depicts a perspective view of a 3D printing nozzle, in accordance with embodiments of the present invention;

FIG. 2D depicts a front view of the 3D printing nozzle of FIG. 2C;

FIG. 2E depicts a cross-sectional view of the 3D printing nozzle along section A-A of FIG. 2D;

DETAILED DESCRIPTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure.

As a preface to the detailed description, it should be noted that, as used in this specification and the appended claims, the singular forms "a", "an" and "the" include plural referents, unless the context clearly dictates otherwise.

Figures 1A, 1B:
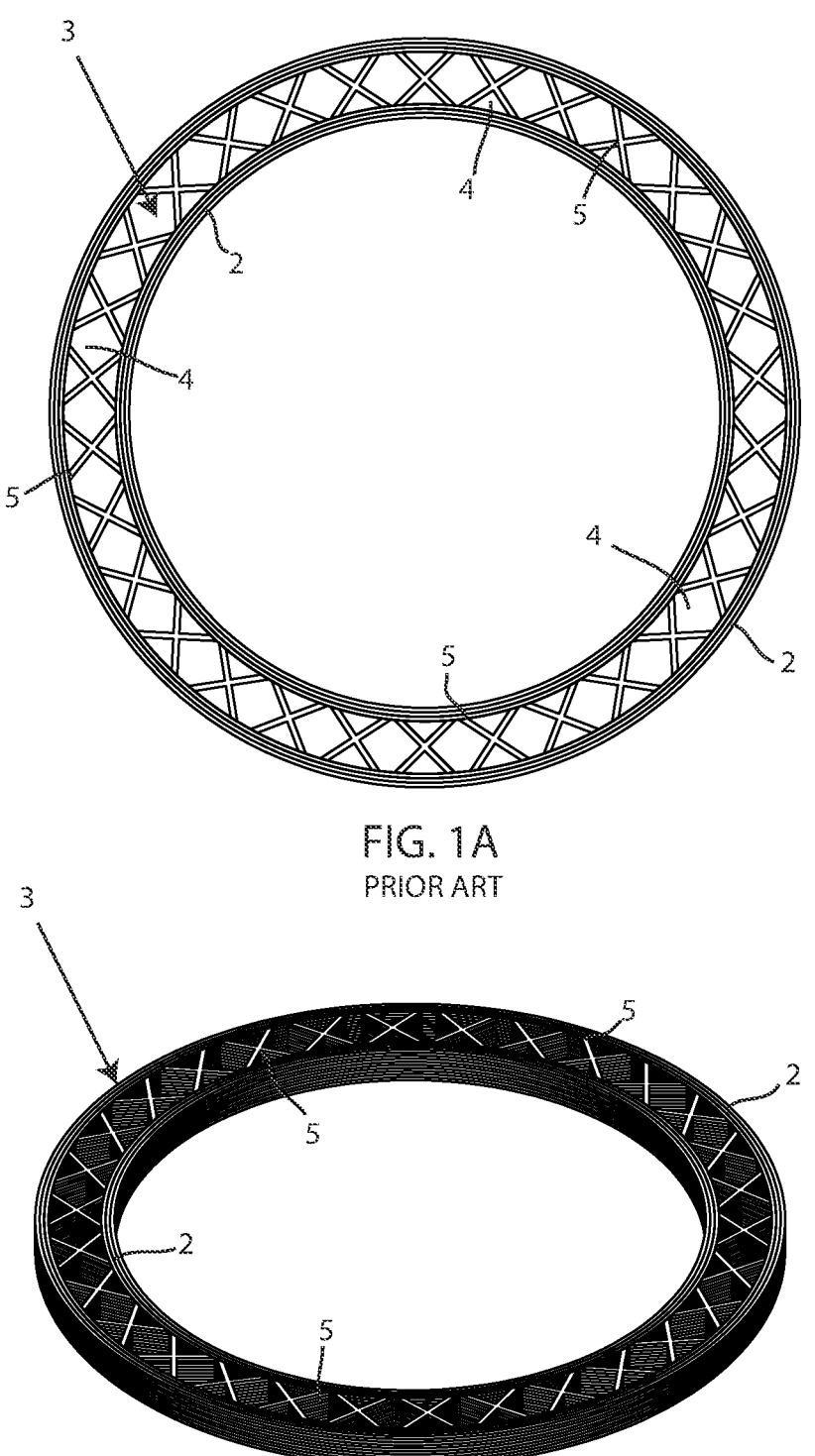
FIG. 1A depicts a 3D printed wall perimeter printed with conventional 3D printing methods.
FIG. 1B depicts a perspective view of the 3D printed wall perimeter of FIG. 1A.

In brief overview, prosthetic sockets accommodate a residual limb of a user, and are customized to the shape of the user's limb. Prosthetic sockets that are 3D printed according to conventional methods using conventional printing nozzles lack clarity to visualize the user's limb while the printed prosthetic socket is tested on the user's limb. For example, even if optically clear printing material is used, multiple internal layers forming a wall of the prosthetic socket and connection points between the internal layers cause light passing through to be refracted in a manner that prevents or significantly hinders visibility through the prosthetic socket. FIGS. 1A and 1B depict a 3D printed wall perimeter printed with conventional 3D printing methods. Wall 3 is formed of multiple internal layers 2 forming an exterior portion of the wall 3 and an interior portion of the wall 3. In the example shown in FIGS. 1A and 1B, the exterior portion of the wall 3 includes at least three separate layers that are each associated with a pass of the printing nozzle, and the interior portion of the wall 3 also includes at least three separate layers that are each associated with a pass of the printing nozzle. The exterior portion of the wall 3 and the interior portion of the wall 3 are connected by a plurality of connection points 5. The presence of the connection points 5 and the multi-layer wall sections 2 causes light to be refracted such that the wall 3 is not transparent. In other words, the wall 3 of the prosthetic socket is not clear enough for a visual inspection of the user's residual limb within the prosthetic socket.

Furthermore, prosthetic sockets that are 3D printed according to conventional methods using conventional printing nozzles require additional components to increase a strength of the printed socket. Additional strength is necessary for attachment to metal hardware connecting the socket to a pylon structure of the prosthetic assembly. These additional components must be attached to the socket after the socket is printed, which requires additional time to prepare the socket for use with the user, and adds costs and complexity to the prosthetic assembly. One of the reasons conventional 3D printed sockets lack the requisite structural strength is the wall perimeter of the socket is full of voids 4, which either need to be infilled with material and/or supported by external elements attached to the body of the socket. The presence of the voids 4 create structural weak points in the socket construction that lead to buckling under the weight of the user and/or during attachment to the pylon structure of the prosthetic assembly.

Figure 1C:
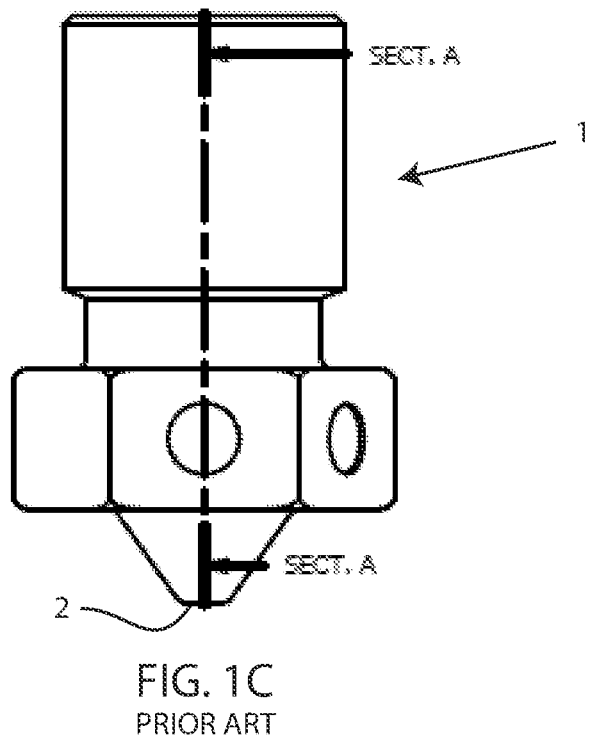
FIG. 1C depicts a conventional 3D printing nozzle.
Figure 1D:
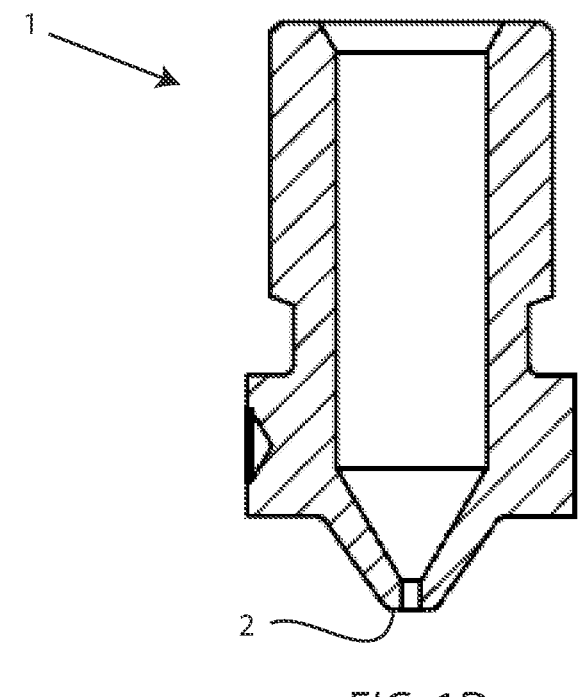
FIG. 1D depicts a cross-sectional view along section A-A of the conventional 3D printing nozzle of FIG. 1C.

The wall construction of conventional prosthetic sockets which leads to poor clarity and structural weaknesses are due to the relatively small width of each pass of a conventional 3D printing nozzle. FIGS. 1C and 1D depict a conventional 3D printing nozzle 1 having a nozzle face 2 that limits the width of a deposited printing material during each pass of the nozzle 1. For instance, conventional 3D printing nozzles typically have an outlet diameter ranging from 0.15 mm to 1 mm, and a nozzle face diameter ranging from 0.3 mm to 2.0 mm, including the diameter of the outlet. The solid surface portion of the nozzle face 2 can be used to disperse the deposited printing material but only to a width equal to the width of the nozzle face 2. The width of the nozzle face 2 of conventional nozzle 1 is too small to form a single, solid wall perimeter of a 3D printed socket capable of being transparent and bearing a user's weight and/or attach to pylon hardware. Conventional 3D printing methods for creating prosthetic sockets using the conventional nozzle 1 require several passes within the same layer to form a minimally acceptable perimeter wall thickness. Consequently, the printed prosthetic is not clear enough for proper visual inspection and lacks the strength for quick attachment to a pylon.

Figure 2A:
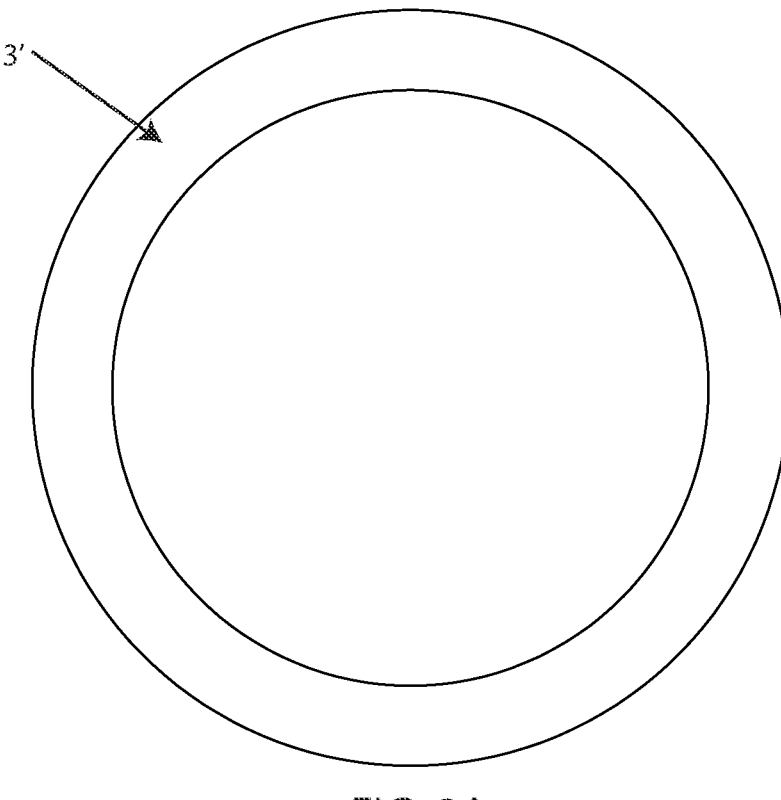
FIG. 2A depicts a 3D printed solid wall perimeter printed with 3D printing methods in accordance with embodiments of the present invention.
Figure 2B:
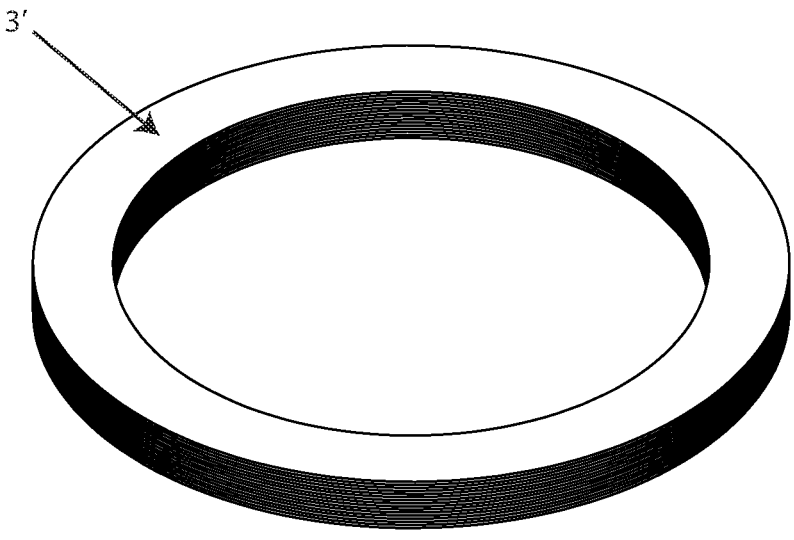
FIG. 2B depicts a perspective view of the 3D printed solid wall perimeter of FIG. 2A.

Embodiments of the present invention describe a 3D printing method that can 3D print a prosthetic socket that is optically clear for visual inspection of the user's residual limb while the user is testing/wearing the prosthetic socket, requires no additional support elements, and is immediately ready for attachment to the pylon and use by a user. FIGS. 2A and 2B depict a solid wall perimeter 3' printed with 3D printing methods in accordance with embodiments of the present invention. The solid wall perimeter 3' does not include multiple, separate wall layers and connection points between the wall layers that cause light to refract and hinder or prevent visibility through the wall. Instead, the single, solid wall 3' allows a sufficient amount of light to pass through so that the prosthetic socket is transparent/clear. The clarity of prosthetic sockets printed according to embodiments of the invention is advantageous because a clinician can visually observe the user's residual limb within the prosthetic socket as the user wears the prosthetic socket. For instance, pressure points between the user's residual limb and the prosthetic socket can be visually observed through the wall of the prosthetic socket to ensure a comfortable fit for the user. Moreover, the solid wall perimeter 3' does not include voids that require infill so the socket construction is stronger than sockets printed using conventional 3D printing methods and nozzles. The solid wall perimeter 3' avoids voids or air gaps which may form using conventional 3D printing methods between an inner wall edge and an outer wall edge. Further, the solid wall perimeter 3' does not have to be continuous in a circumferential direction in every embodiment. For instance, at a specific height above the bottom surface, the wall may have a gap in the circumferential direction while remaining a solid wall construction in the radial direction where the wall is present. As an example, a bore may extend through the body of the socket or a recess may be present in the body of the socket, resulting in a gap in a circumferential direction at those locations, while the wall construction is solid.

In alternative embodiments, the prosthetic socket can be printed with any suitable 3D printing material, for example, a printing material that is not optically clear, using the printing techniques described herein, such as the solid wall, single pass technique. For example, the printing material may be any color and/or any opacity that does not necessarily result in a transparent socket wall. While using printing material that is colored, dark, opaque, or otherwise not considered optically clear can impact the transparency of the printed socket and the advantages associated therewith, printing a solid wall with a single pass as described herein using a non-optically clear printing material still results in a structurally sound, 3D printed prosthetic socket. Therefore, 3D printing a prosthetic socket using a non-optically clear material according to the methods of 3D printing described herein is possible.

The solid wall perimeter 3' is printed with a width achieved in a single pass of a printing nozzle. To achieve the required width to form a solid wall in a single pass, a surface area of a nozzle face of a 3D printing nozzle is significantly increased compared to the surface area of the nozzle face 2 of the conventional nozzle 1 shown in FIGS. 1C-D. Instead of having a sharply tapered nozzle that results in a small nozzle face, embodiments of the present invention use a 3D printing nozzle with an enlarged nozzle face.

FIGS. 2C-2E depict an embodiment of a 3D printing nozzle 10, in accordance with embodiments of the present invention. The nozzle 10 includes a nozzle body 11 having a fluidic pathway 13 therethrough and an outlet 14 disposed at an end of the nozzle body 11. The nozzle 10 also includes an enlarged nozzle face 12 adjacent to the outlet opening 13 of the nozzle body 11. The nozzle 11 with the enlarged nozzle face 12 produces a print width much larger than a diameter of the filament used for printing the prosthetic socket. The extent to which the nozzle face 12 is enlarged is based on the diameter of the filament used in the printing process. In other words, the diameter of the nozzle face 12 is tied to the diameter of the filament, such that the diameter of the nozzle face 12 is greater than the diameter of the filament being used. In an exemplary embodiment, the diameter of the nozzle face 12 is at least 1.45 times larger than the diameter of the filament being used. In another exemplary embodiment, the diameter of the nozzle face 12 is between 1.45 and 2.25 times larger than the diameter of the filament being used. In another exemplary embodiment, the diameter of the nozzle face 12 is between 1.45-5 times larger than the diameter of the filament being used. In yet another exemplary embodiment, the diameter of the nozzle face 12 is more than 5 times larger than the diameter of the filament being used.

Optionally, the nozzle face 12 is enlarged with respect to the rest of the components of the nozzle 11. For instance, the nozzle face 12 is enlarged but the size of the nozzle, size of the orifice, the diameter of the orifice, etc. can remain the same. As an example, the nozzle 11 can be configured for a 1.75 mm or 2.8 mm diameter filament but the diameter of the nozzle face 12 is increased to achieve larger widths per pass of the nozzle 11.

The nozzle face 12 includes a flat surface that is used to manipulate the deposited printing material to achieve a desired width or thickness. For example, the nozzle face 12 of the nozzle 10 physically contacts the deposited printed material to disperse the deposited printing material to a width that is greater than the outlet opening of the nozzle 10. Because the nozzle face 12 is oversized compared to conventional nozzles, a limit to the width of deposited printing material achieved in a single pass of the nozzle 10 is increased. The increased width limit allows for the printing of a single, solid wall perimeter without voids and multiple layers that harm the clarity of wall. The single, solid wall perimeter construction significantly increases clarity of 3D printed prosthetic sockets. To add strength to the 3D printed prosthetic socket, a plurality of stiffener elements are formed as a function of the printing the solid wall perimeter (i.e. with a single pass of the nozzle 10). The stiffener elements provide enough strength to the printed prosthetic socket for attachment to a metal pylon/pipe/structure, while maintaining an internal geometry of the socket that contacts the user's residual limb which is critical for comfort.

Figure 3:
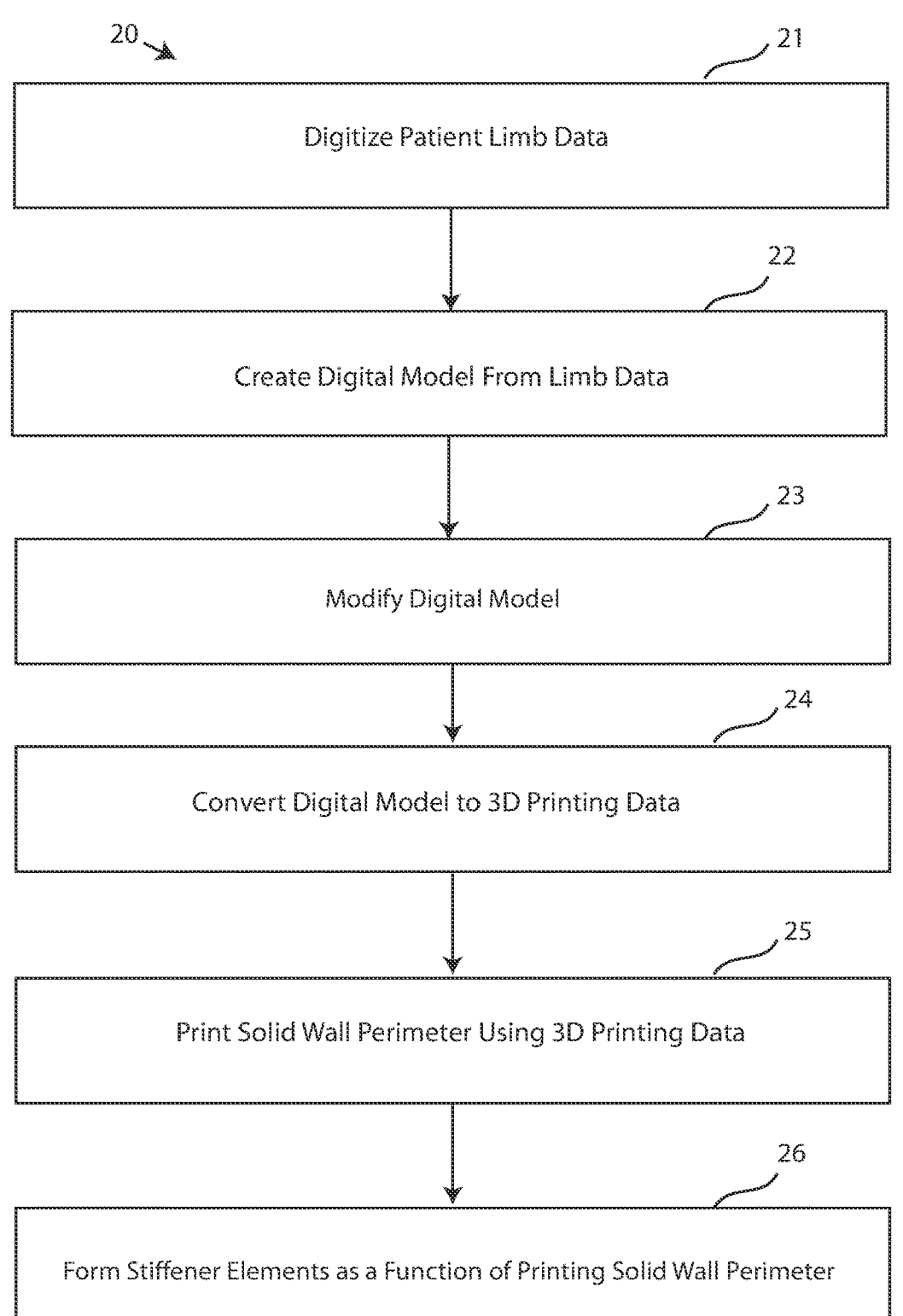
FIG. 3 depicts a flowchart of a method for 3D printing a prosthetic socket, in accordance with embodiments of the present invention.

Referring still to the drawings, FIG. 3 depicts a flowchart of a method for 3D printing a prosthetic socket from a digital model, in accordance with embodiments of the present invention. The method begins with the step 21 of digitizing the specific anthropomorphic data of the residual limb of a user. The limb data can be digitized by scanning the residual limb, scanning a physical cast of the limb, or manually measuring the residual limb and entering the measurements. Step 22 creates a digital model from the limb data. Conventional software can be used to develop the digital model, including directly from a 3D/structural scanner if used in step 21. Step 23 modifies the digital model. Once the digital model is created, computer-aided design (CAD) or computer-aided engineering (CAE) software can be utilized to develop a customized socket from the digital model, having custom internal and external geometries. For example, using software, the digital model can be modified to include a desired number of stiffener elements, a shape of the stiffener elements, a location of the stiffener elements, and the like. Step 24 converts the digital model into an appropriate language or protocol for manufacturing by a 3D printer or CAM machine. As an example, an acceptable conventional language is G-code and accounts for the particular machine/filament combination, ideal extrusion temperature, extrusion rate/speed, build plate temperature, and tool path.

Figure 4:
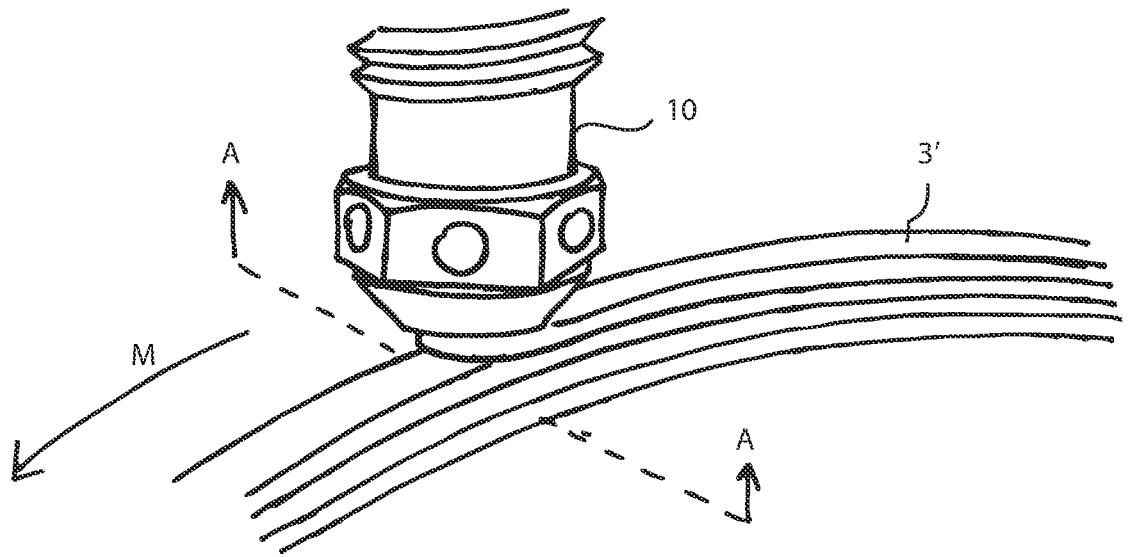
FIG. 4 depicts a schematic representation of the 3D printing method, in accordance with embodiments of the present invention.
Figure 5:
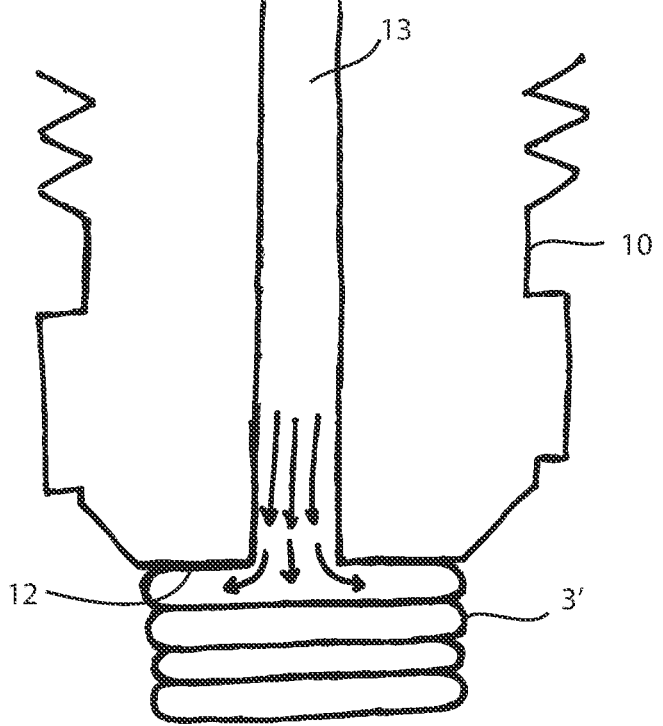
FIG. 5 depicts a cross-sectional view along section A-A of FIG. 4.

Using the printing data, step 25 prints a solid wall perimeter of the prosthetic socket. The solid wall of the socket can be printed either in sequential layers or as a continuous spiral known as vase mode. The solid wall perimeter of the prosthetic socket can have a varying thickness but each layer of the solid wall is free of voids. For example, the thickness of the wall depends on the volumetric flow rate of the printing material through the printing nozzle and/or a height of the printing nozzle from an existing printed layer. Further, the size of the nozzle face of the printing nozzle can also determine the width of each pass of the printing nozzle. As described supra, the enlarged nozzle face 12 of the printing nozzle 10 allows the deposited material to be dispersed at least as wide as the nozzle face 12 in a single pass of the nozzle 10. FIGS. 4 and 5 depict a schematic representation of printing the solid wall perimeter 3' of the prosthetic socket, in accordance with embodiments of the present invention. As shown, the nozzle 10 moves in direction M to deposit a printing material to form the layered solid perimeter wall 3'. The nozzle 10 may continuously move in direction M to form the wall 3' (e.g. vase mode), or the nozzle 10 may move in direction M to form a discrete layer, move up, and then move in direction M again or opposite direction M to deposit another discrete layer on top of the previous layer so that the wall 3' is formed in sequential layers. As the printing material exits the fluidic pathway 13 at the outlet, the nozzle face 12 disperses the printing material to achieve a full width of a layer in a single pass of the nozzle 10. Because the full width of the perimeter wall 3' is formed in a single pass of the nozzle 10, the perimeter wall 3' is considered to a solid with no voids, connection points, or intermediate layers forming the wall 3'. The resultant perimeter wall 3', which is printed with a clear printing material, remains clear after the wall 3' is printed so that the user's residual limb can be observed through the wall 3'. The wall 3' is optionally coated for additional clarity.

Figure 6:
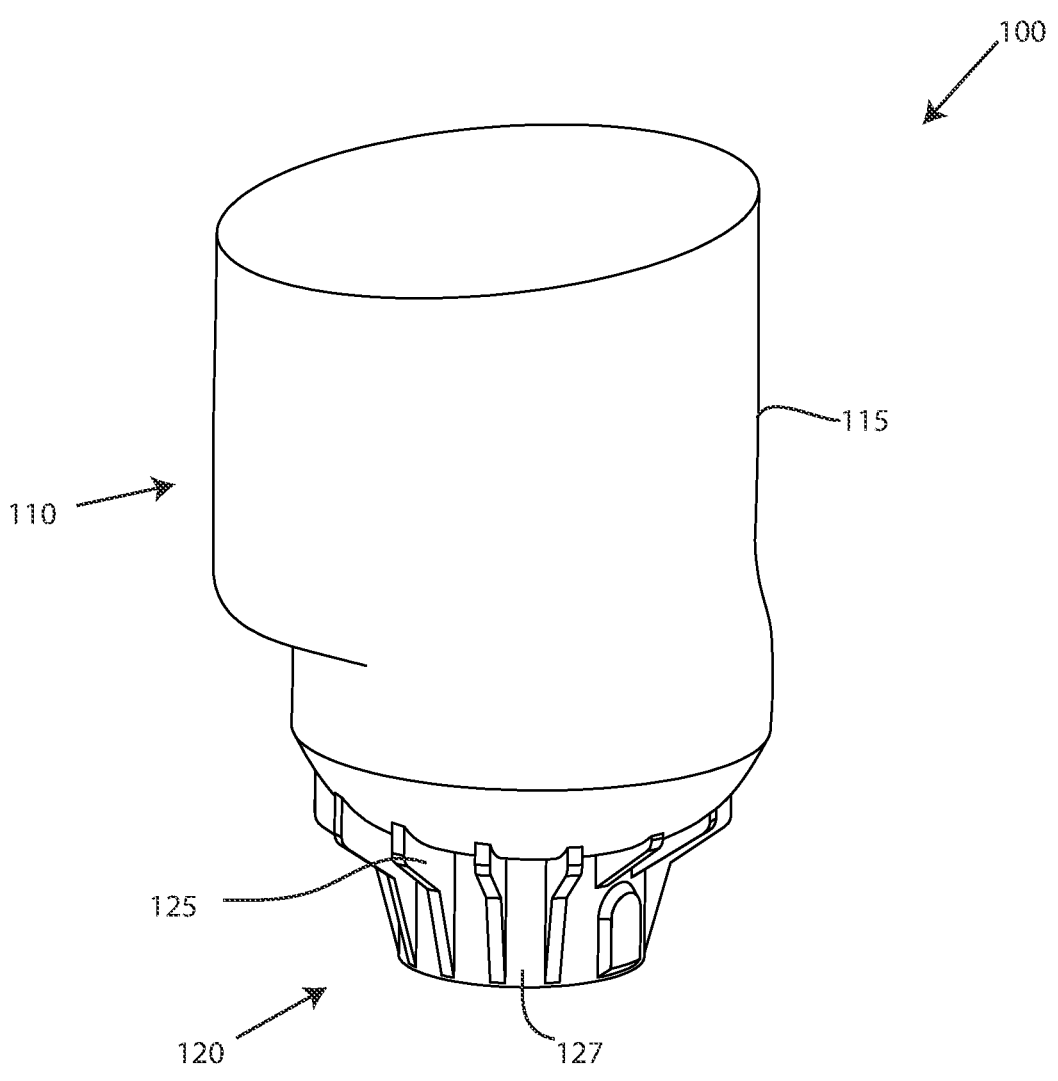
FIG. 6 depicts a 3D printed prosthetic socket with stiffener elements, in accordance with embodiments of the present invention.

As a function of printing the solid wall perimeter 3', stiffener elements are formed during step 26. Stiffener elements provide additional strength to the socket proximate a lower portion of the socket. Moreover, the stiffener elements are structurally integral with the solid wall perimeter of the socket and are formed in a single pass of the printing nozzle. FIG. 6 depicts a 3D printed prosthetic socket 100 with stiffener elements 125, manufactured in accordance with embodiments of the present invention. The internal geometry of the socket 110 is determined based on the shape of the residual limb of the user. The external geometry may be varied depending on strength requirements of the socket 100, while maintaining the internal geometry critical for the user's comfort. The socket 100 includes an upper portion 110, a lower portion 125, and a plurality of stiffener elements 125. The upper portion 110 and the lower portion 120 are structurally integral with each other and formed as part of the same 3D printing sequence building the solid perimeter wall 115. The lower portion 120 is configured to be attached to a prosthetic pylon. The plurality of stiffener elements 125 extend from the lower portion 120. For instance, the stiffener elements 125 radially extend from an exterior surface 127 of the lower portion 120 of the socket 100. In some embodiments, the stiffener elements 125 are disposed circumferentially around the lower portion 120 of the prosthetic socket 100. Further, the stiffener elements 125 are positioned vertically on the lower portion 120 of the socket 100, each having a thickness achievable by a single pass of the printing nozzle. The stiffener elements 125 may be ribs, fins, extensions, and the like.

Figure 7:
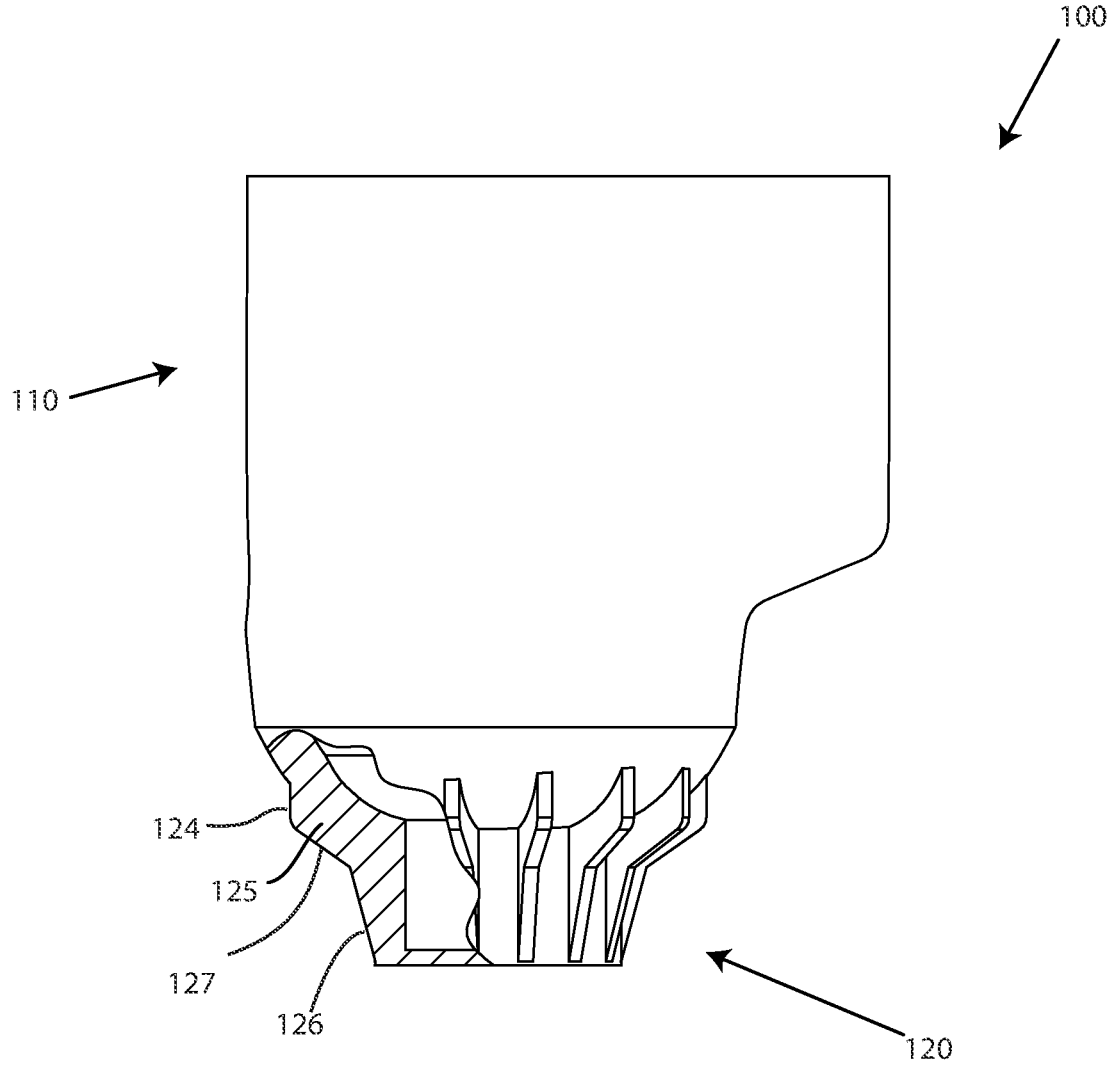
FIG. 7 depicts a partial cut-away view of a stiffener element of the 3D printed prosthetic socket of FIG. 6.

The upper portion 110, the lower portion 120, and the plurality of stiffener elements 125 are printed as a solid wall construction comprised of a printing material deposited using only a single pass of a printing nozzle. FIG. 7 depicts a partial cut-away view of a stiffener element 125 of the 3D printed prosthetic socket 100 of FIG. 6. As shown, the stiffener element 125 is a solid construction, thereby providing structural strength to the prosthetic socket 100. The radial extension of each stiffener element 125 may gradually increase as the prosthetic socket 100 is being printed. In the exemplary embodiment of FIG. 7, the stiffener element 125 tapers at more than one rate measured from a bottom edge of the socket 100. Proximate the bottom surface, the stiffener element 125 has a first tapered section 126 that tapers at a first rate and a second tapered section 127 adjacent to the first tapered section 126 that tapers at a different rate than the first tapered section 126. The rate that the second tapered section 127 is more acute than the rate of the taper of the first tapered section 126. A vertical section 124 is adjacent to the second tapered section 127.

Figure 8A:
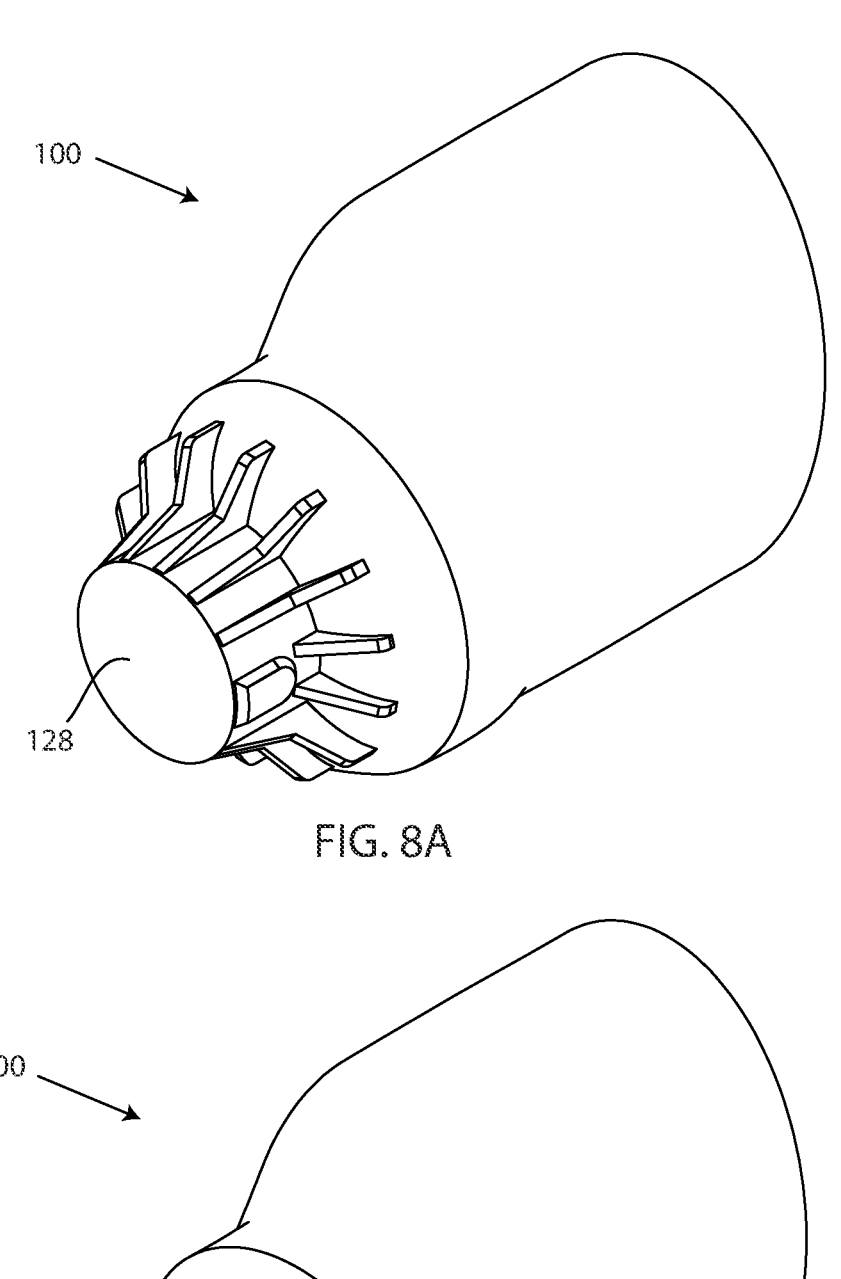
FIG. 8A depicts a bottom, perspective view of the 3D printed prosthetic socket with stiffener elements, in accordance with embodiments of the present invention.
Figure 8B:
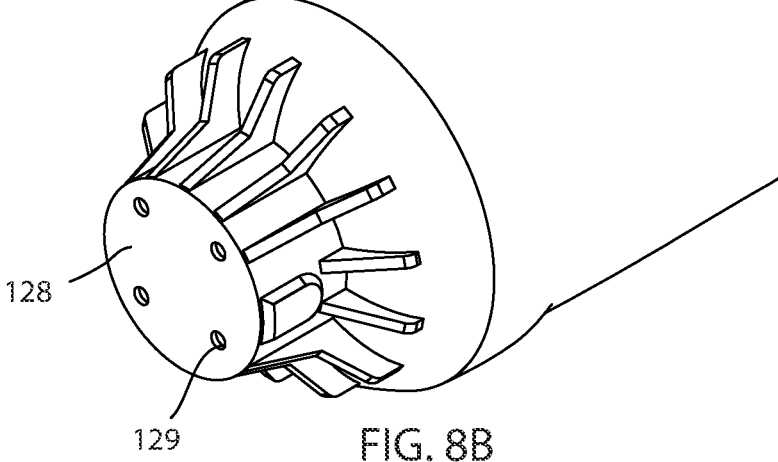
FIG. 8B depicts a bottom, perspective view of the 3D printed prosthetic socket with stiffener elements and holes for mounting to prosthetic hardware, in accordance with embodiments of the present invention.

FIG. 8A depicts a bottom, perspective view of the 3D printed prosthetic socket 100 with stiffener elements 100, in accordance with embodiments of the present invention. As shown, the prosthetic socket 100 includes a bottom surface 128 which is typically the first layer formed by the printing nozzle during manufacture of the prosthetic socket 100. The bottom surface 128 is flat and sized and dimensioned to accommodate mounting hardware for mounting the pylon structure to the prosthetic socket 100. FIG. 8B depicts a bottom, perspective view of the prosthetic socket 100 with holes 129 for mounting prosthetic hardware to the socket 100. The holes 129 are configured to receive fasteners to attach the mounting hardware to the prosthetic socket 100. The number of holes 129 and the size of the holes 129 can vary depending on the type of mounting hardware and the recommended method of attaching the mounting hardware. In one embodiment, the bottom surface 128 is printed as a solid surface and holes 129 are formed after the prosthetic socket 100 is printed, using known methods for drilling holes through a 3D printed object. In another embodiment, the prosthetic socket 100 is printed with the holes 129. In yet another embodiment, the bottom surface 128 of the prosthetic socket 100 does not include holes and the mounting hardware is adhered to the bottom surface 128 of the prosthetic socket 100 without the need for holes.

Figures 9A, 9B, 9C:
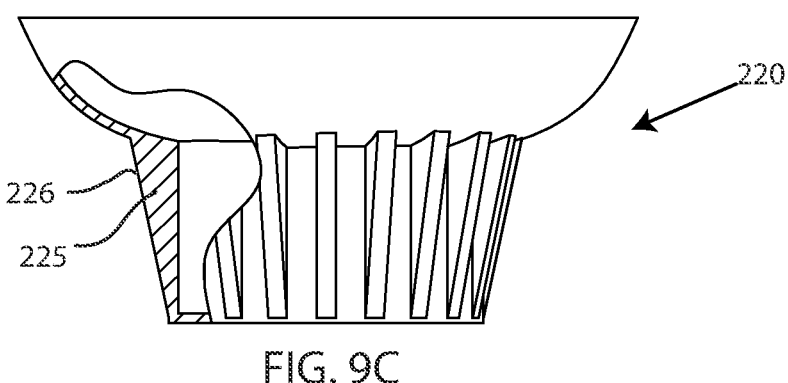
FIG. 9A depicts a 3D printed prosthetic socket with an alternative configuration of stiffener elements, in accordance with embodiments of the present invention.
FIG. 9B depicts a bottom, perspective view of the 3D printed prosthetic socket of FIG. 9A.
FIG. 9C depicts a partial cut-away view of a stiffener element of the 3D printed prosthetic socket of FIG. 9A.

Alternative embodiments of the prosthetic socket can be manufactured using the unique a method described herein. For example, various configurations of stiffener elements can be designed and printed as a single, solid wall construction. FIGS. 9A-9C depict a 3D printed prosthetic socket 200 with an alternative configuration of stiffener elements 225. Similar to prosthetic socket 100, embodiments of prosthetic socket 200 include an upper portion 210, a lower portion 220, and a plurality of stiffener element 225. The shape of the stiffener elements 225 are different than the stiffener elements 125 of prosthetic socket 100. Here, the stiffener elements 225 include a single tapered section 226 that gradually increases from a bottom surface to a curved position of the upper portion 210.

Figure 10A:
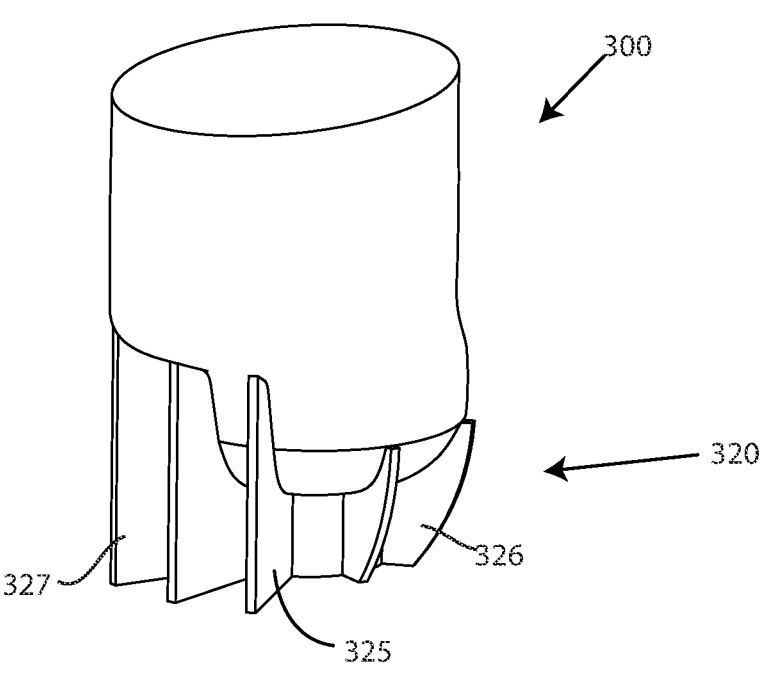
FIG. 10A depicts a 3D printed prosthetic socket with another alternative configuration of stiffener elements, in accordance with embodiments of the present invention.
Figure 10B:
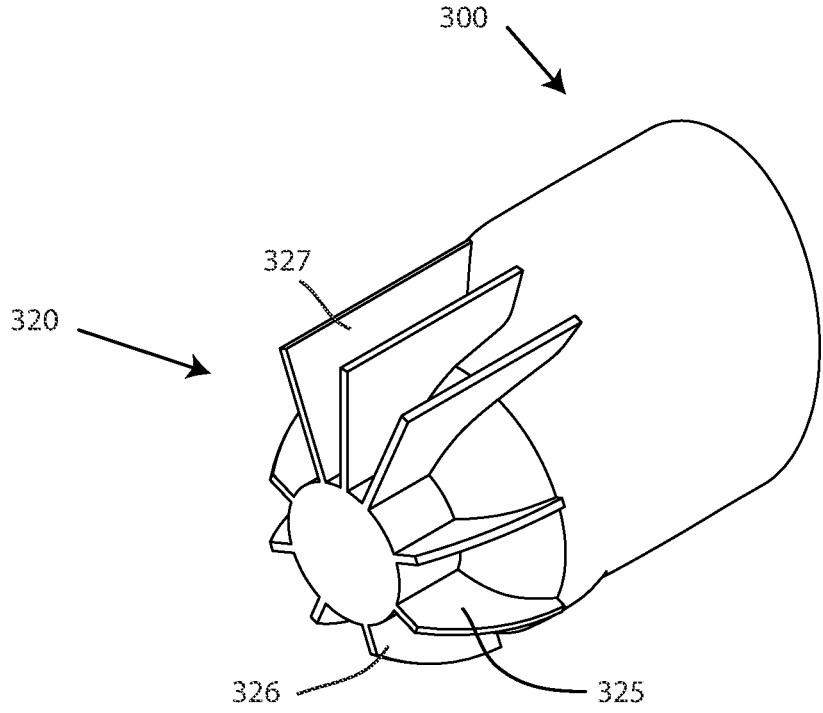
FIG. 10B depicts a bottom, perspective view of the 3D printed prosthetic socket of FIG. 10A.

FIGS. 10A and 10B depict a 3D printed prosthetic socket with another alternative configuration of stiffener elements 325. Similar to prosthetic socket 100, 200 embodiments of prosthetic socket 300 include an upper portion 310, a lower portion 320, and a plurality of stiffener element 325. In this configuration, not all of the stiffener elements 325 are the same size or shape, and the stiffener elements 325 are a different shape than the stiffener elements 125, 225 of socket 100, 200, respectively. Here, the stiffener elements 325 include a first type of stiffener element 326 and a second type of stiffener element 327. The first type of stiffener element 326 radially extends from the lower portion 320 and has a curved outermost edge that terminates at or proximate the beginning of the upper portion 310 of the prosthetic socket 300. The second type of stiffener element 327 radially extends from the lower portion 320 and has a straight outermost edge that extends beyond the lower portion 320 and terminates at some point in the upper portion 310, well above the other stiffeners 326.

Figure 11A:
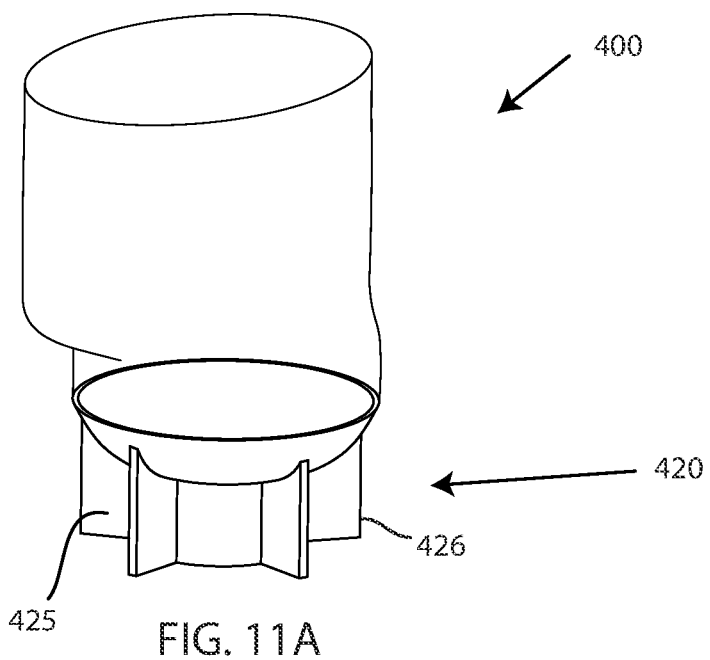
FIG. 11A depicts a 3D printed prosthetic socket with another alternative configuration of stiffener elements, in accordance with embodiments of the present invention.
Figure 11B:
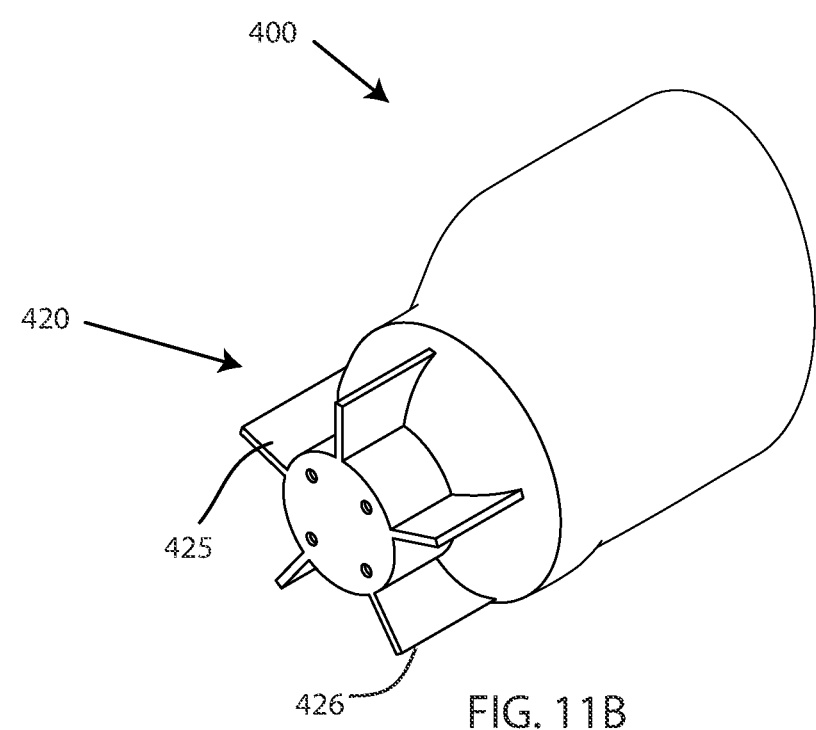
FIG. 11B depicts a bottom, perspective view of the 3D printed prosthetic socket of FIG. 11A.

FIGS. 11A and 11B depict a 3D printed prosthetic socket 400 with another alternative configuration of stiffener elements 425. Similar to prosthetic socket 100, 200, 300 embodiments of prosthetic socket 400 include an upper portion 410, a lower portion 420, and a plurality of stiffener element 425. In this configuration, all of the stiffener elements 425 are the same size and shape, but the stiffener elements 425 are a different shape than the stiffener elements 125, 225, 325 of socket 100, 200, 300, respectively, and there are fewer total stiffener elements 425. Here, the stiffener elements 425 radially extend from the lower portion 420 and have a straight outermost edge that terminates at or proximate the beginning of the upper portion 410 of the socket 400.

Although only a few variations of the stiffener elements are shown herein, many different configurations are possible that can be optimized for providing structural strength to the lower portion of the socket. The size, shape, rate of taper, lack of taper, distance of radial extension, thickness, distance of vertical extension, a number of stiffener elements, and the like can be varied and printed in many different configurations, without affecting the internal geometry of the socket while affording the requisite structural strength proximate the lower portion of the socket.

Figures 12A, 12B:
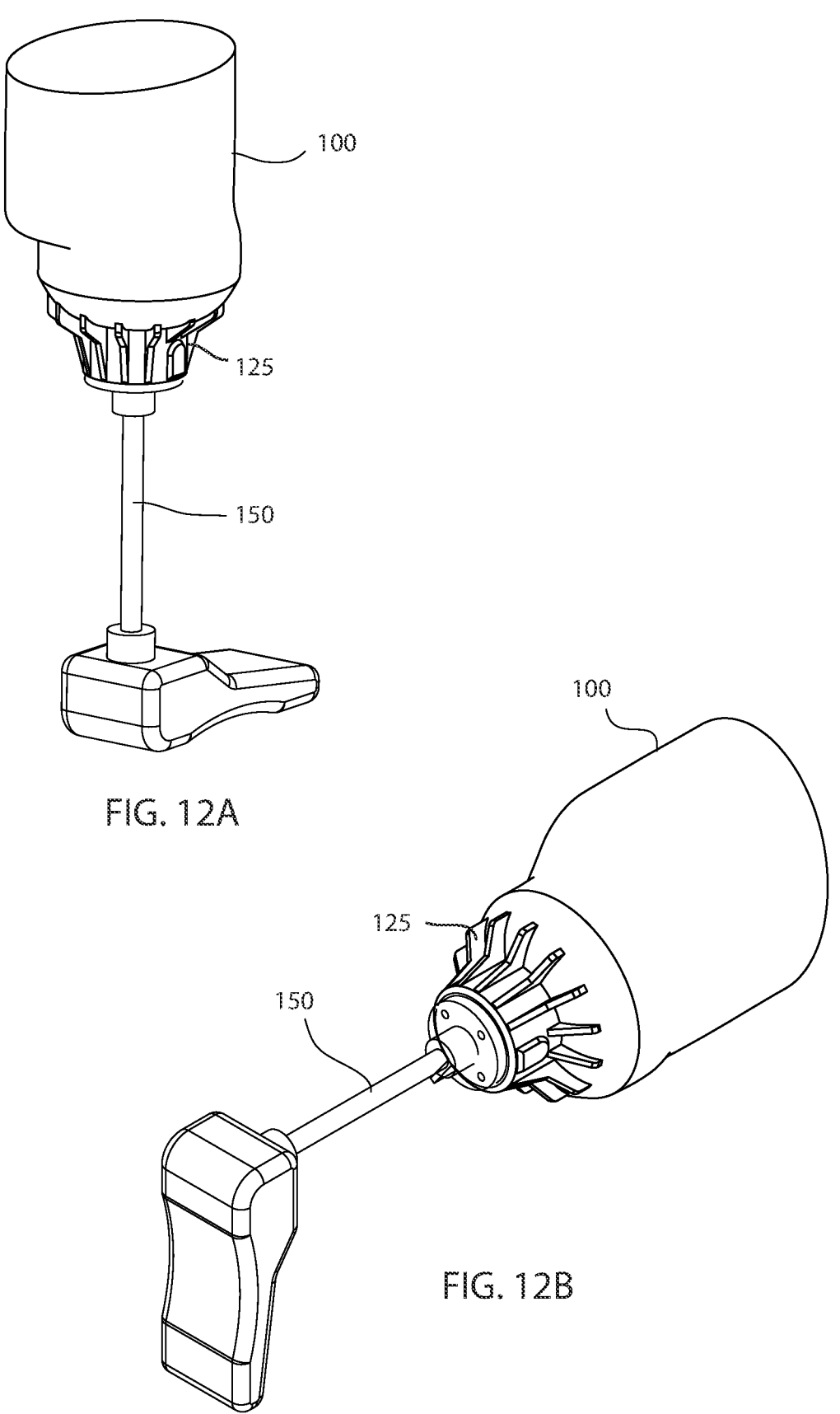
FIG. 12A depicts a 3D printed socket attached to a prosthetic pylon, in accordance with embodiments of the present invention.
FIG. 12B depicts a bottom, perspective view of a 3D printed socket attached to a prosthetic pylon, in accordance with embodiments of the present invention.

Referring still to the drawings, FIGS. 12A and 12B depict a 3D printed prosthetic socket 100 attached to a prosthetic pylon 150, in accordance with embodiments of the present invention. Due to the single, solid wall construction of the prosthetic socket 100 which includes at least one stiffener element 125 as part of the single, solid wall construction, the prosthetic socket 100 can be 3D printed and be immediately ready for attachment to the pylon 150 and use by the user. Additionally, because the prosthetic socket 100 is transparent, the fit of the prosthetic socket 100 can be visually observed.

Embodiments of the prosthetic socket 100, 200, 300, 400 can be 3D printed with a variety of different printing materials. In an exemplary embodiment, the prosthetic socket 100, 200, 300, 400 is printed with an optically clear material, such as is a transparent polycarbonate, polyethylene terephthalate glycol (PETG), polycylcohexylendimethylene terephthalate glycol (PCTG), polyactic acid (PLA), nylon, acrylonitrile butadiene styrene (ABS), polypropylene, and polyetherimide (PEI) based filaments.

While this disclosure has been described in conjunction with the specific embodiments outlined above, it is evident that many alternatives, modifications and variations will be apparent to those skilled in the art. Accordingly, the preferred embodiments of the present disclosure as set forth above are intended to be illustrative, not limiting. Various changes may be made without departing from the spirit and scope of the invention, as required by the following claims. The claims provide the scope of the coverage of the invention and should not be limited to the specific examples provided herein.

What is claimed is:

1. A method for 3D printing a prosthetic socket from a digital model, comprising:
   printing a solid wall perimeter of the prosthetic socket with a width achieved in a single pass of a printing nozzle; and
   forming a plurality of stiffener elements proximate a bottom end of the prosthetic socket, as a function of the printing the solid wall perimeter.

2. The method of claim 1, wherein the solid wall perimeter is printed in sequential layers.

3. The method of claim 1, wherein the solid wall perimeter is printed in a vase mode.

4. The method of claim 1, wherein the solid wall perimeter is transparent.

5. The method of claim 1, wherein the solid wall perimeter is entirely comprised of an optically clear printing material.

6. The method of claim 5, wherein the optically clear printing material is a transparent polycarbonate, polyethylene terephthalate glycol (PETG), polycylcohexylendimethylene terephthalate glycol (PCTG), polyactic acid (PLA), nylon, acrylonitrile butadiene styrene (ABS), polypropylene, and polyetherimide (PEI) based filament.

7. The method of claim 1, further comprising: dispersing a deposited printing material using the printing nozzle to achieve a desired thickness of the solid wall perimeter in the single pass.

8. The method of claim 1, further comprising: coating a surface of the prosthetic socket.

9. A 3D printed prosthetic socket comprising:
   an upper portion;
   a lower portion configured to be attached to a pylon; and
   a plurality of stiffener elements radially extending from an exterior surface of the lower portion;
   wherein the upper portion, the lower portion, and the plurality of stiffener elements are printed as a solid wall construction comprised of a printing material deposited using only a single pass of a printing nozzle.

10. The 3D printed prosthetic socket of claim 9, wherein the plurality of stiffener elements are disposed circumferentially around the lower portion.

11. The 3D printed prosthetic socket of claim 9, wherein each of the plurality of stiffener elements are a same shape.

12. The 3D printed prosthetic socket of claim 9, wherein a portion of the plurality of stiffener elements are a different shape than another portion of the plurality of stiffener elements.

13. The 3D printed prosthetic socket of claim 9, further comprising a bottom surface of the lower portion having at least one opening configured to receive hardware for fastening the 3D printed prosthetic socket to the prosthetic pylon.

14. The 3D printed socket body of claim 9, wherein the upper portion, the lower portion, and the plurality of stiffener elements are comprised of an optically clear material.

15. The 3D printed prosthetic socket of claim 9, wherein an external geometry of the socket is variable while maintain an internal geometry of the socket.

* * * * *